United States Patent [19]
Balkwill

[11] Patent Number: 5,279,586
[45] Date of Patent: Jan. 18, 1994

[54] REUSABLE MEDICATION DELIVERY PEN
[75] Inventor: David Balkwill, Nantes, France
[73] Assignee: Becton, Dickinson and Company, Franklin Lakes, N.J.
[21] Appl. No.: 831,141
[22] Filed: Feb. 4, 1992
[51] Int. Cl.$^5$ .............................................. A61M 5/00
[52] U.S. Cl. ................................... 604/207; 604/211; 604/218; 604/232; 222/43; 222/46; 222/48; 222/336; 222/309
[58] Field of Search ........................................ 604/187, 218, 224, 207-211, 232, 246, 157, 222/386, 390, 391, 46-48, 43, 309, 336

[56] References Cited

U.S. PATENT DOCUMENTS

| | | | |
|---|---|---|---|
| 4,086,062 | 4/1978 | Itoch | 222/43 X |
| 4,395,921 | 8/1983 | Oppenlander | 222/43 X |
| 4,592,745 | 6/1986 | Rex et al. | 604/211 |
| 4,865,591 | 9/1989 | Sams | 604/186 |
| 4,883,472 | 11/1989 | Michel | 604/208 |
| 4,936,833 | 6/1990 | Sams | 604/232 |
| 4,968,299 | 11/1990 | Ahlstrand et al. | 604/90 |
| 4,973,318 | 11/1990 | Holm et al. | 604/208 |
| 5,017,190 | 5/1991 | Simon et al. | 604/207 |
| 5,085,352 | 2/1992 | Sasaki et al. | 222/327 |
| 5,092,842 | 3/1992 | Bechtold et al. | 604/135 |
| 5,112,317 | 5/1992 | Michel | 604/208 |

Primary Examiner—C. Fred Rosesnbaum
Assistant Examiner—Mark O. Polutta
Attorney, Agent, or Firm—John L. Voellmicke

[57] ABSTRACT

An injection device medication delivery pen is provided for injecting fluids such as insulin within body tissue. The device includes a housing, a piston rod movably mounted within the housing, and a dose setting mechanism for controlling the movement of the piston rod with respect to a fluid containing cartridge removably positioned within the housing. The piston rod includes a plunger and a lead screw slidably positioned within the plunger. The plunger and lead screw are coupled by a pair of half nuts. The half nuts may be uncoupled from the lead screw in order to allow it to slide freely with respect to the plunger. A new cartridge may accordingly be installed quickly and easily as the lead screw is easily displaced by a new cartridge.

10 Claims, 8 Drawing Sheets

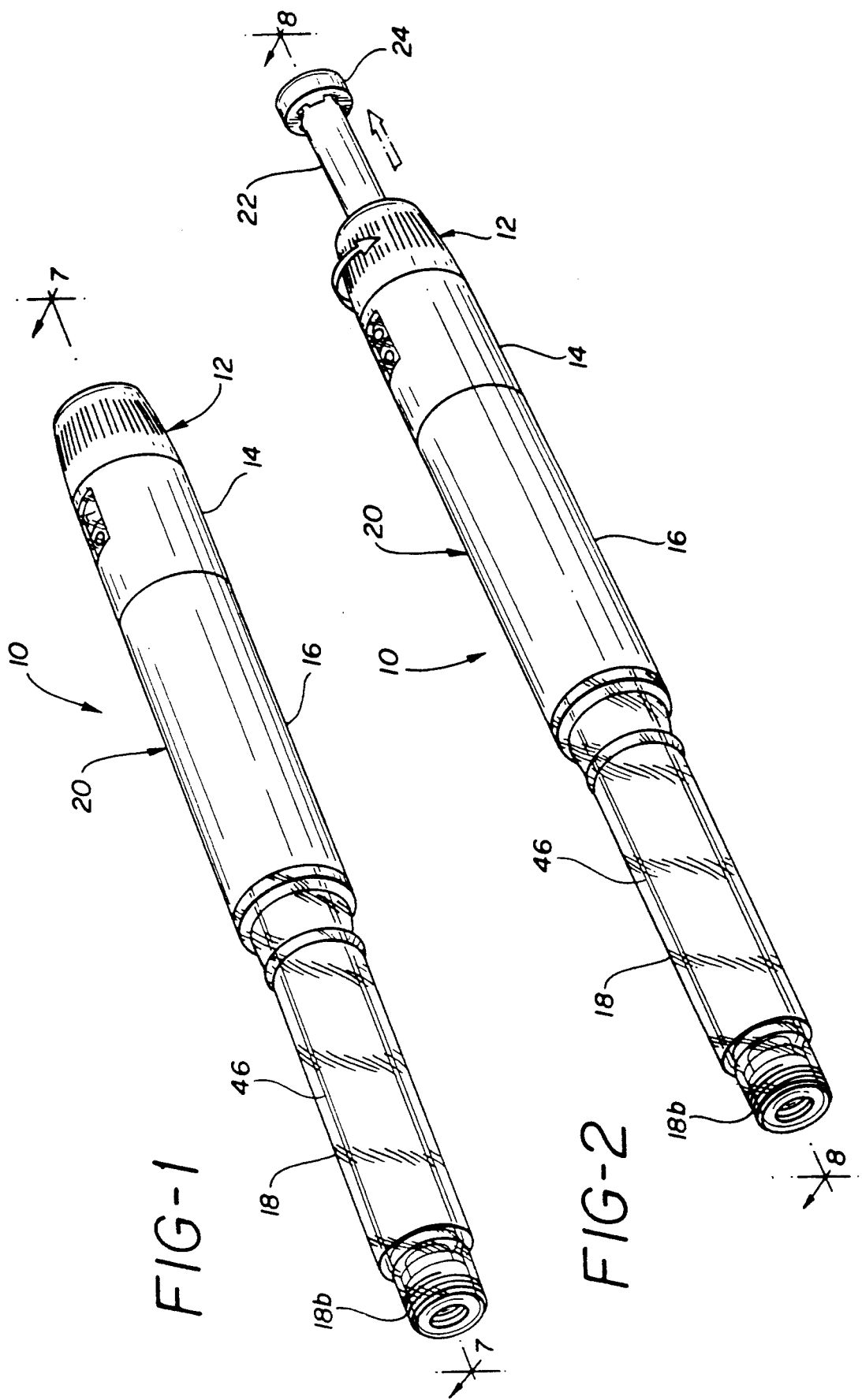

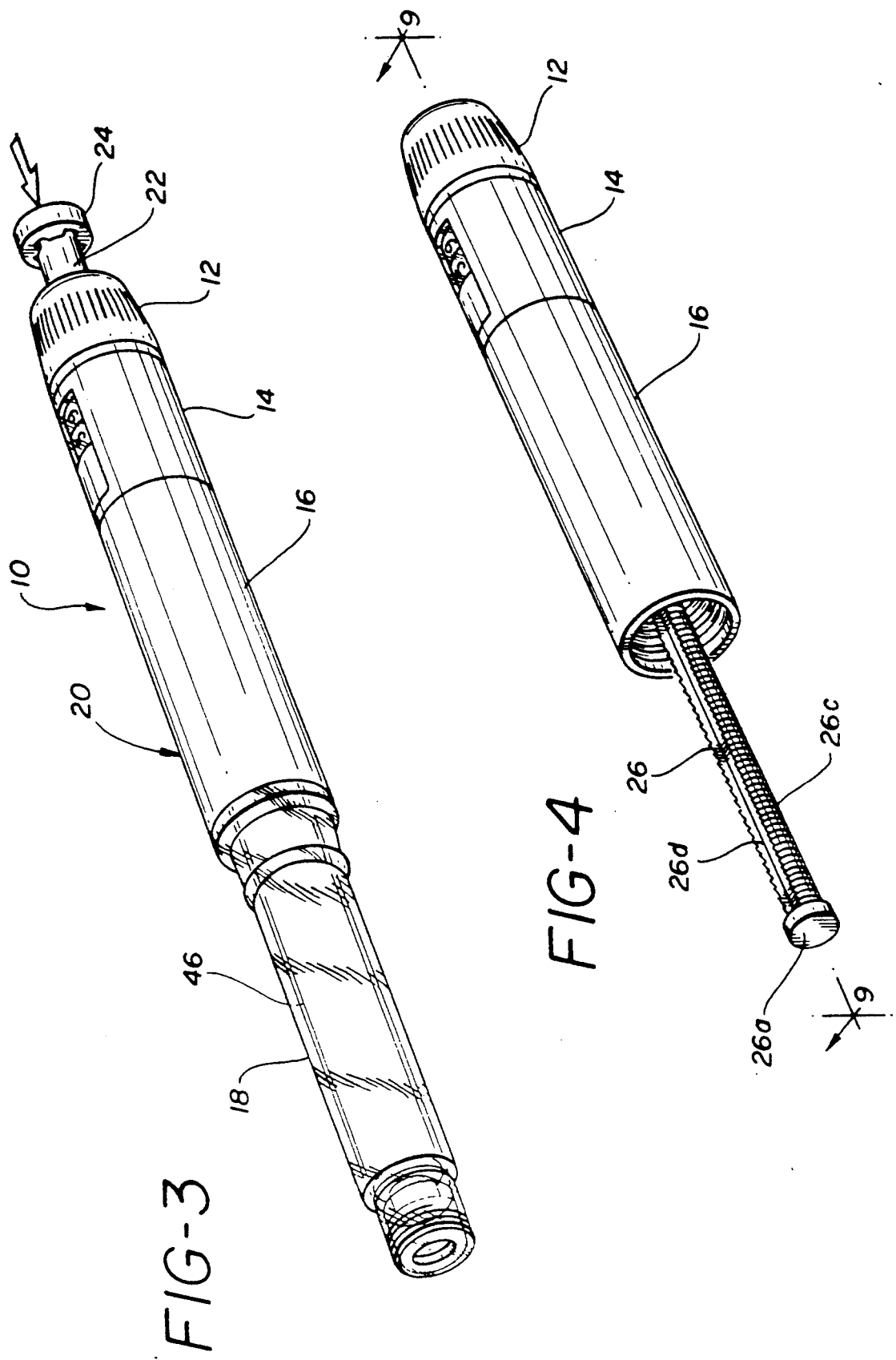

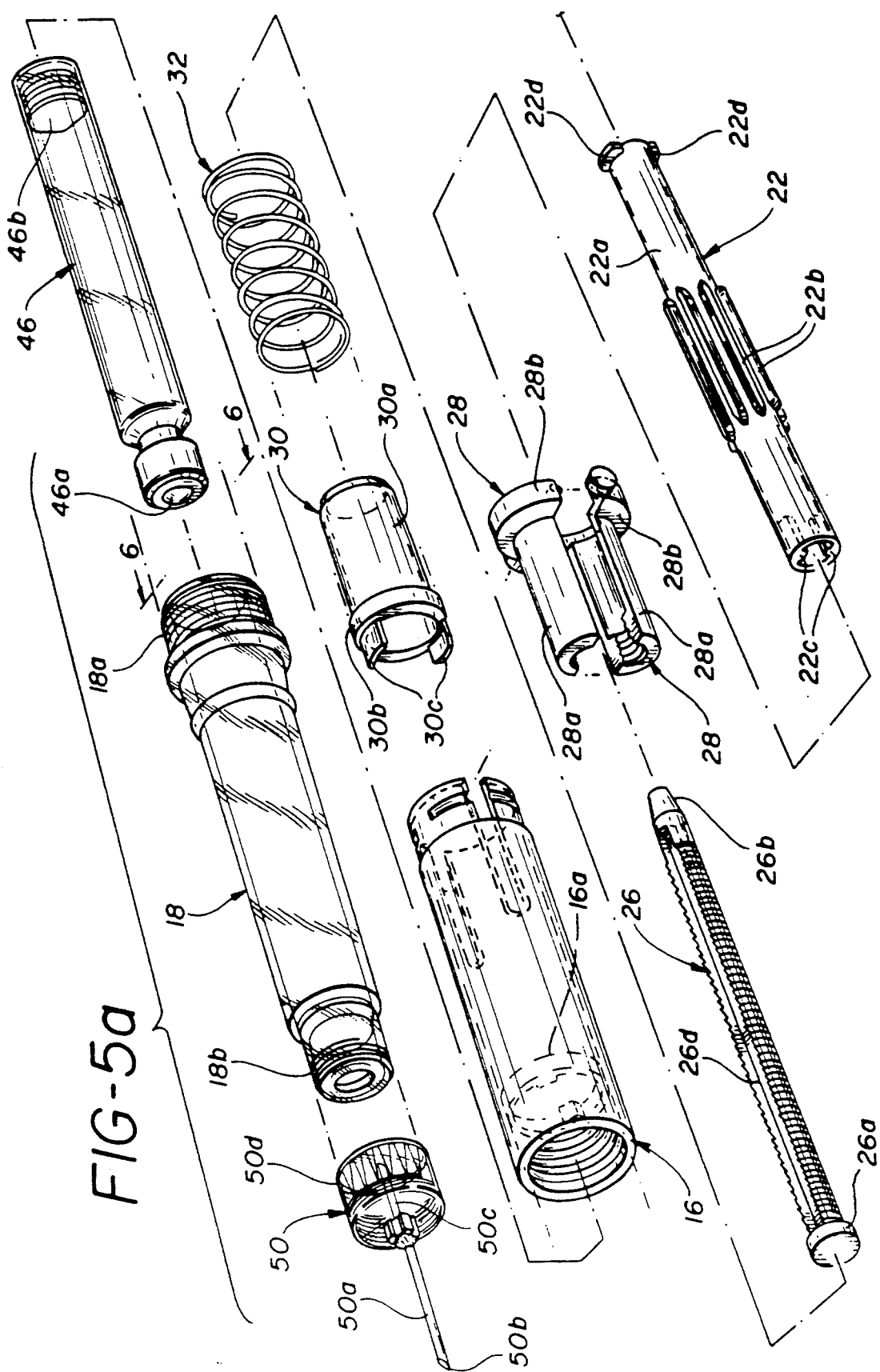

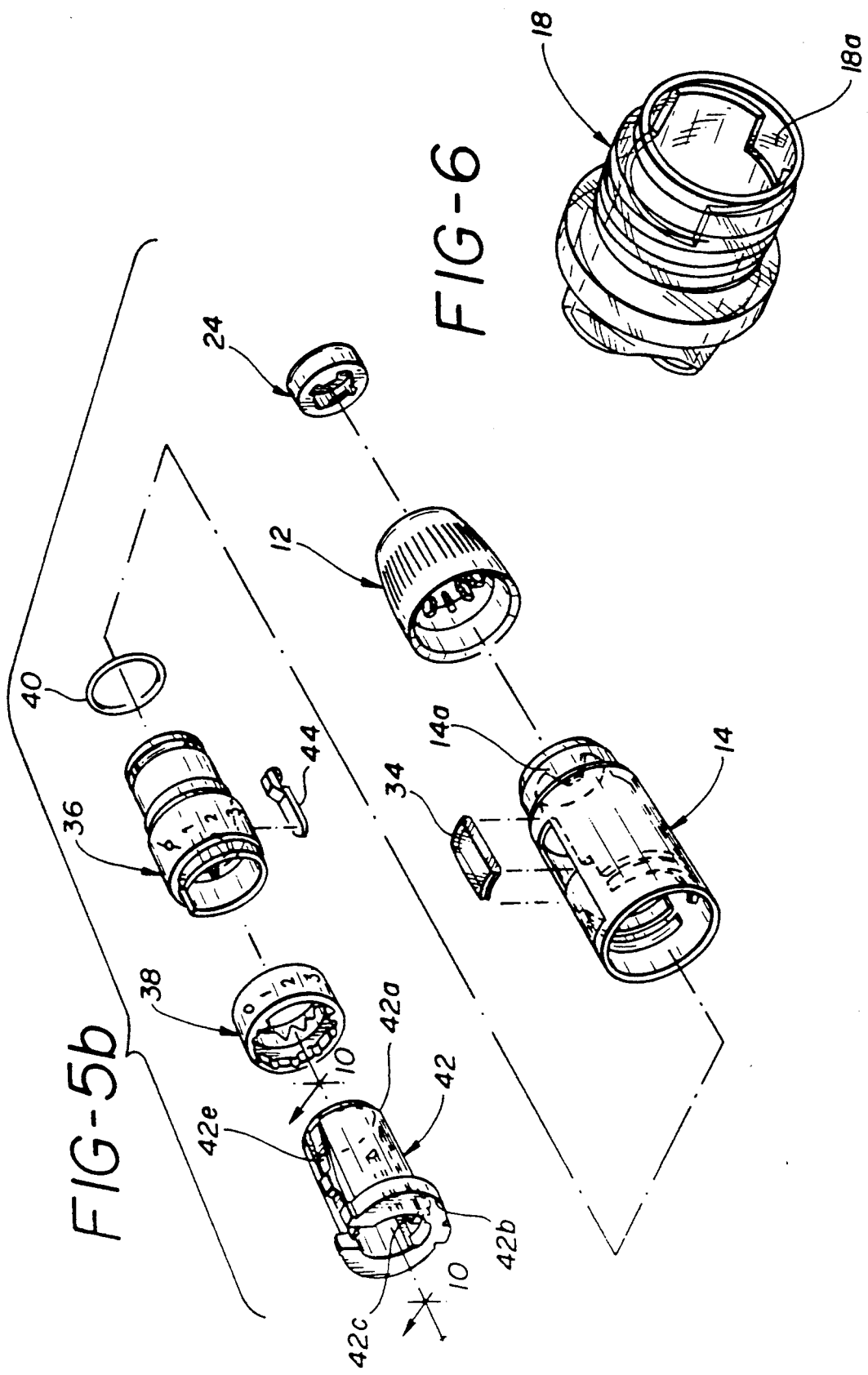

REUSABLE MEDICATION DELIVERY PEN

BACKGROUND OF THE INVENTION

1. Field of the Invention

The field of the invention relates to medication delivery pens including dosage setting means.

2. Brief Description of the Related Art

A number of devices have been developed for administering insulin, drugs or other substances to persons and animals. As self administration of certain substances, such as insulin, is common, it is important that devices designed for self-administration be simple to operate, reliable and accurate.

U.S. Pat. No. 4,883,472 discloses an injection device which is capable of dispersing the contents of a pre filled cartridge by advancing the piston within the cartridge by a selected amount. A displacing sleeve is provided for axially displacing a gear element by a constant stroke. The sleeve is moved in the advancing direction against the force of a spring, and is moved back to a rest position by the spring. A threaded rod may be axially advanced with respect to the gear element in order to set the desired dosage. The rod engages the cartridge piston when the sleeve is advanced, thereby advancing the piston by a selected distance corresponding to the selected dosage.

U.S. Pat. No. 4,865,591 discloses another injection device which, unlike that disclosed in U.S. Pat. No. 4,883,472, controls the dosage by allowing the stroke of a drive member to be varied. The distance traveled by the drive member corresponds to that traveled by the piston within an insulin cartridge. The dosage is displayed through a port in the body of the pen. The port is positioned adjacent to a scale including indicia corresponding to dosage units.

U.S. Pat. No. 4,973,318 discloses another injection device in which the dosage administered corresponds to the distance traveled by the actuating member. A coarse dosage indicator is centrally located on the device, and provides an indication of smaller dosage units.

U.S. Pat. No. 5,017,190 discloses an injection device including a circumferential measuring scale which provides an indication of the individual steps of a ratchet as adjustment means are turned. A longitudinal measuring scale is provided on a piston rod and indicates the dosage amount.

SUMMARY OF THE INVENTION

An injection device for injecting selected dosages of fluid of the present invention includes an elongate housing, a plunger positioned at least partially within the housing and a lead screw positioned at least partially within the plunger and axially slidable therein. The injection device includes means for threadably engaging the lead screw and means for selectively moving the means for threadably engaging the lead screw into and out of engagement with the lead screw so that the lead screw is freely slidable with respect to the plunger when the means for threadably engaging the lead screw is disengaged from the lead screw. The lead screw and the plunger are slidable as a unit with respect to the housing when the means for threadably engaging the lead screw is engaged with the lead screw. The device further includes means for securing a cartridge for containing fluid to the housing. This means for securing a cartridge is engageable with the means for selectively moving so that the lead screw is disengaged from the means for threadably engaging the lead screw when the means for securing the cartridge is disengaged from the housing.

BRIEF DESCRIPTION OF THE DRAWINGS

FIG. 1 is a perspective view of an injection device according to the invention;

FIG. 2 is a perspective view thereof showing the device in a zero position;

FIG. 3 is a perspective view thereof showing the plunger moving axially during an injection;

FIG. 4 is a perspective view thereof wherein the medication cartridge assembly is removed;

FIGS. 5a and 5b are exploded perspective views of the device shown in FIG. 1 further including a needle assembly;

FIG. 6 is a partially enlarged detailed perspective view of the cartridge housing taken along lines 6—6 as shown in FIG. 5a;

DETAILED DESCRIPTION OF THE INVENTION

Figure 7:
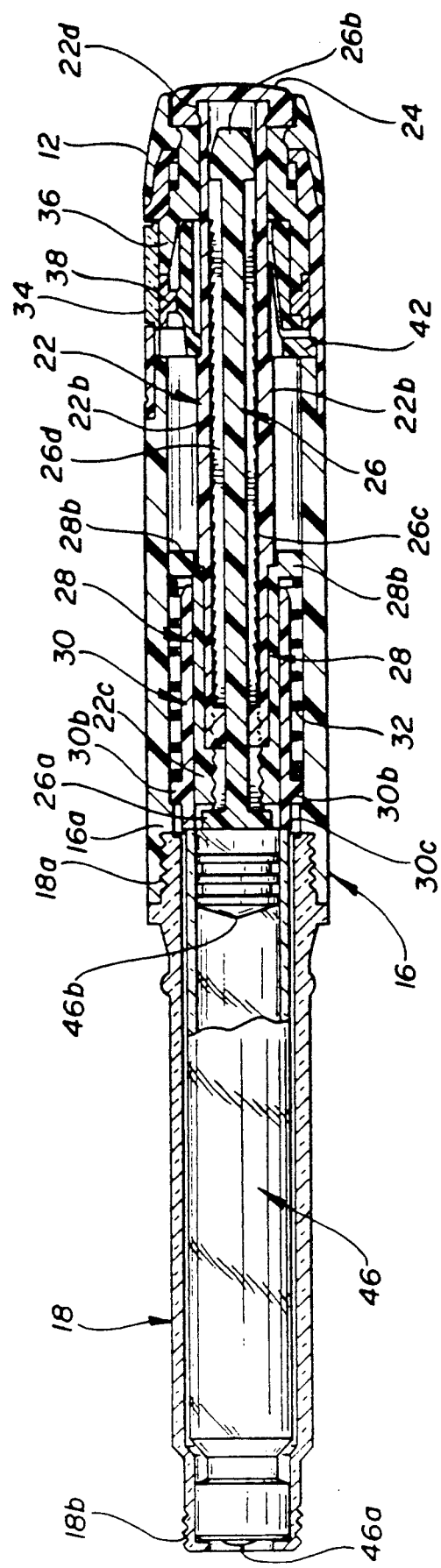
FIG. 7 is a cross sectional view taken along lines 7—7 as shown in FIG. 1.

An injection device 10 for injecting insulin or other medication is provided by the invention. As shown in FIGS. 1-3, the device includes an adjusting knob 12, an upper body 14, a center body 16, and a transparent housing 18. All of these elements have a generally cylindrical configuration, and are arranged coaxially to define a generally cylindrical housing 20 which can easily be handled by a patient or medical attendant.

Referring to FIGS. 1, 5b and 7-9, a plunger 22 is at least partially positioned within the portion of the injection device housing 20 defined by the adjusting knob 12, upper body 14 and center body 16. The plunger includes a hollow, substantially cylindrical body 22a including a band of radially projecting ribs 22b extending outwardly therefrom. A pair of opposing projections 22c extend radially inwardly from the front end of the cylindrical body. The rear end of the plunger includes a pair of projections 22d which extend radially outwardly from the cylindrical body 22a.

The rear end of the plunger 22 is secured to a push button 24. The push button fits partially within the adjusting knob 12 when the plunger is fully inserted within the injection device housing 20.

A lead screw 26 is positioned within and coaxial with the plunger 22. the lead screw includes an enlarged front end 26a and a tapered rear end 26b which are connected by an elongate threaded body 26c. A pair of longitudinal grooves 26d are formed within the threaded body 26c. The grooves 26d receive the radially inwardly extending projections 22c of the plunger 22. The lead screw is accordingly rotatable with the plunger and capable of sliding axially with respect to the plunger.

A pair of half nuts 28 are positioned within the center body 16. Each half nut includes a semi-cylindrical body portion 28a and a radially enlarged end portion 28b. The front end of each half nut is threaded and is ordinarily threadably engaged with the lead screw 26.

The body portions 28a of the half nuts are positioned at least partially within a locking ring 30. The locking ring 30 includes a hollow, generally cylindrical body portion 30a which defines a generally elliptical passage for receiving the half nuts. The front end 30b of the locking ring is radially enlarged. A pair of projections 30c extend axially from the front end of the locking ring. The rear end of the transparent housing 18 (FIG. 6) includes a pair of opposing recesses 18a which are capable of receiving these projections.

A helical coil spring 32 is positioned over the locking ring 30 and half nuts 28. One end of the coil spring bears against the radially enlarged portions 28b of the half nuts while the opposite end thereof bears against the radially enlarged front end 30b of the locking ring. The front end 30b of the locking ring adjoins a radially inwardly extending band 16a on the center body 16. The rear ends of the half nuts abut the ribs 22b of the plunger 22, as shown in FIG. 7.

The upper body 14 includes an opening in which a transparent window 34 is mounted. A units counter ring 36 and a tens counter ring 38 are positioned in adjoining relation beneath the window 34. Both counter rings include outer surfaces including numerals thereon. The numerals are visible through the window.

Figure 8:
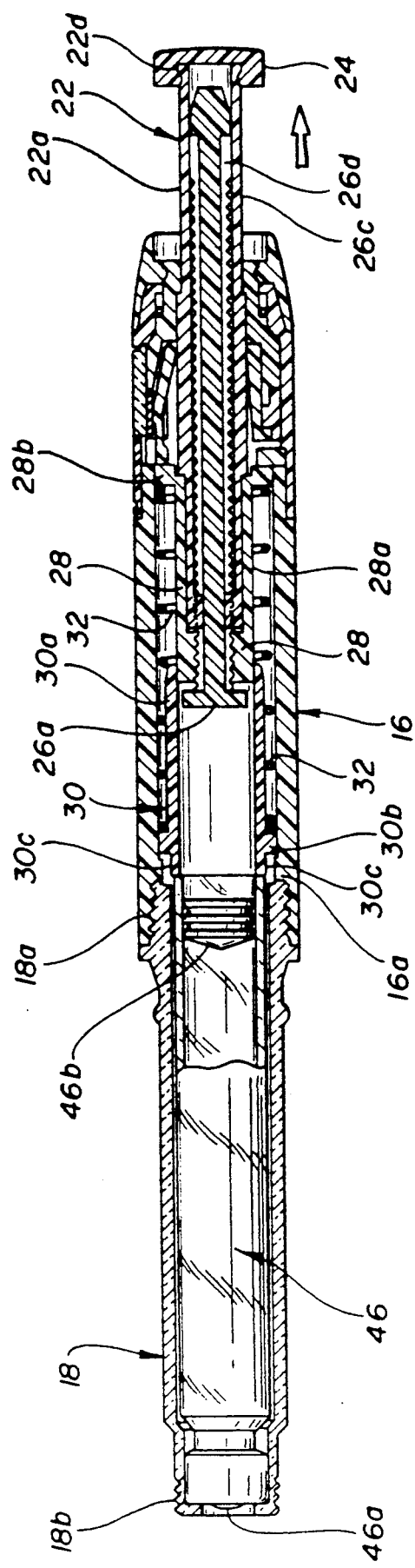
FIG. 8 is a cross sectional view taken along lines 8—8 as shown in FIG. 2.

An O-ring 40 made from an elastomeric material is positioned between the upper body 14 and the units counter ring 36. A zero detection clip 42 is positioned between the inner surfaces of the units and tens counter rings and the outer surface of the plunger 22. The zero detection clip bears against the ribs 22b of the plunger when the spring 32 is in the position shown in FIGS. 7 and 9. It bears against the enlarged end portions 28b of the half nuts when the spring is in the extended position, as shown in FIG. 8.

The inner surface of the units counter ring 36 is splined. This splined surface is engageable with the longitudinal ribs 22b of the plunger, which also function as splines. Such engagement occurs when the spring 32 is in the extended position shown in FIG. 8. The units counter ring 36 is also secured to the adjusting knob 12 such that rotation of the knob causes a corresponding rotation of the counter ring.

Figure 10:
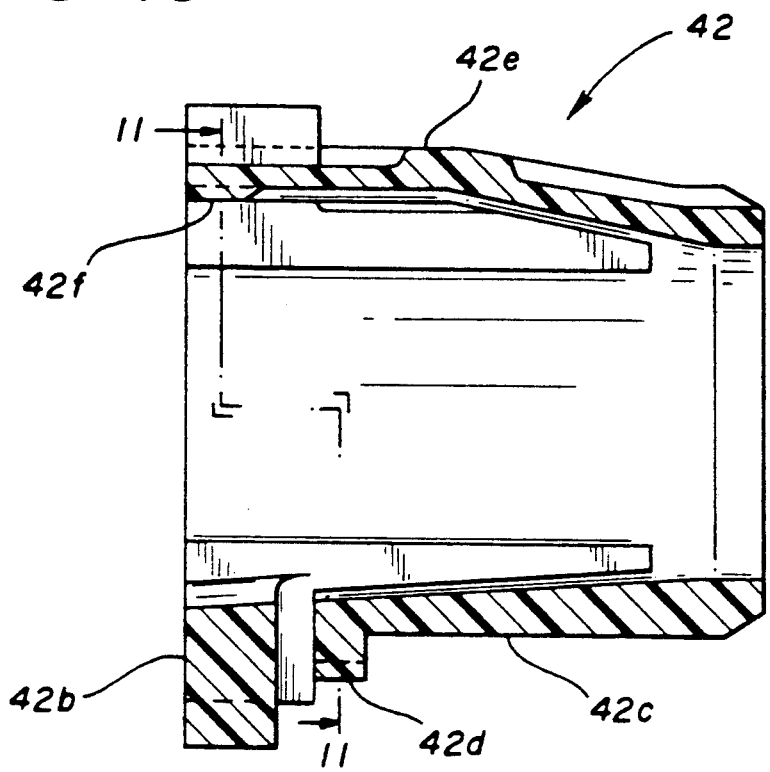
FIG. 10 is an enlarged cross sectional view of a zero detection clip of the device taken along lines 10—10 as shown in FIG. 5b.
Figure 11:
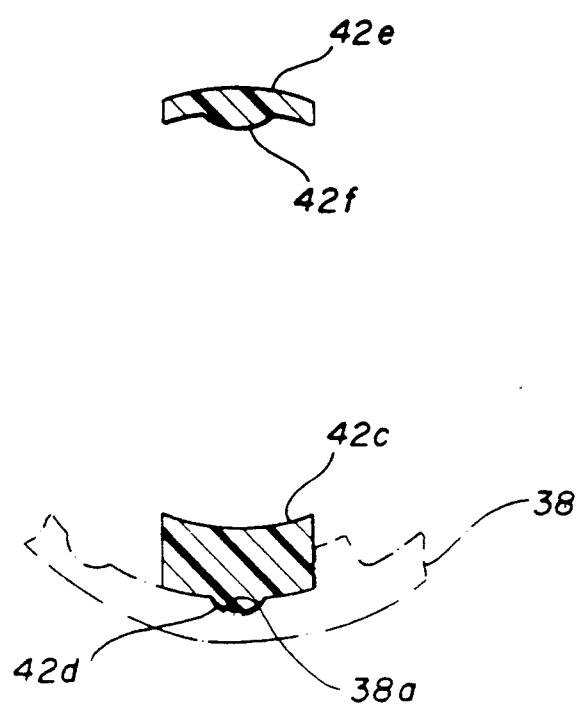
FIG. 11 is a cross sectional view thereof taken along lines 11—11 as shown in FIG. 10.

The zero detection clip 42, as best shown in FIGS. 5b, 10 and 11, includes a generally cylindrical body 42a having a radially enlarged front end 42b. A lower spring member 42c extends axially within a slot formed within the clip body 42a. The lower spring member 42c includes a ridge 42d which is engageable with grooves 38a formed within the inner surface of the tens counter ring 38, as best shown in FIG. 11.

The zero detection clip 42 also includes an axially extending upper spring member 42e, the position of which is controlled by the rotational positions of the units and tens counter rings 36, 38. The upper spring member 42e includes an inner ridge 42f which is engageable with the ribs 22b of the plunger 22 when pushed into its active position by the units counter ring. The inner surface of the units counter ring functions as a cam in controlling the radial position of the upper spring member 42e of the zero detection clip 42.

Figure 9:
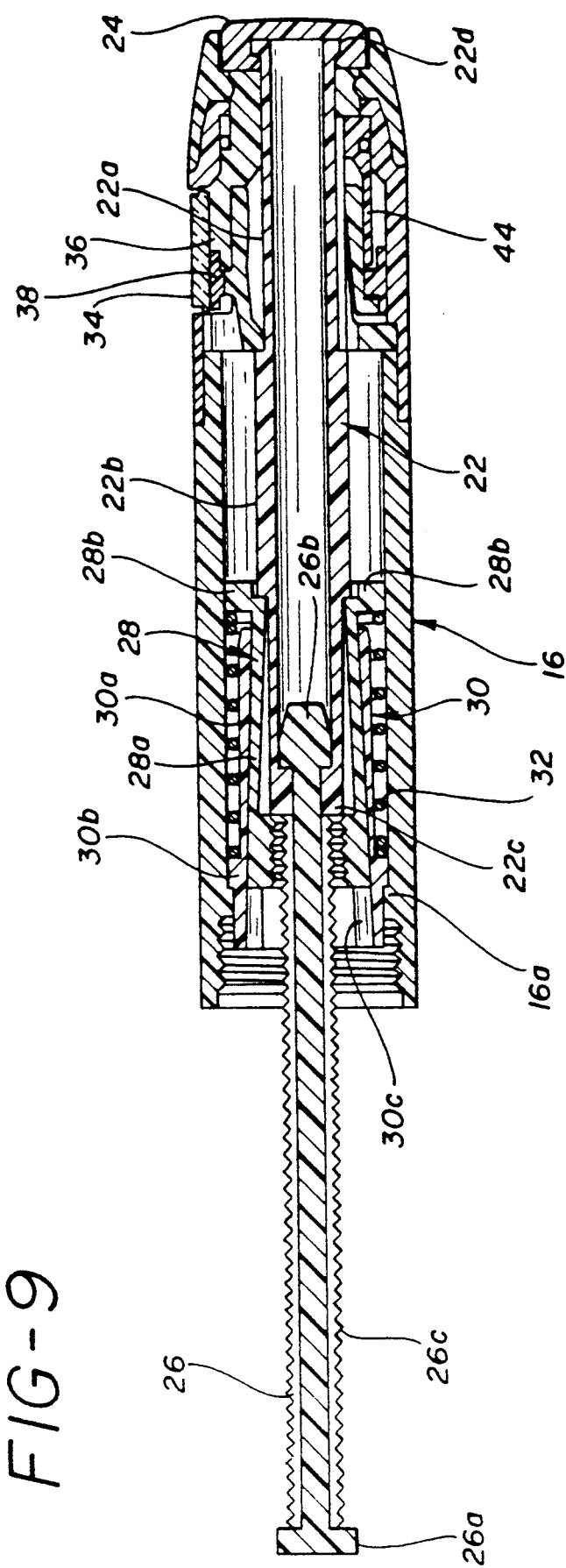
FIG. 9 is a cross sectional view taken along lines 9—9 as shown in FIG. 4.

A transmission key 44 is provided for engaging and disengaging the units and tens counter rings 36, 38. The key is located within a channel formed in the units counter ring, as shown in FIG. 9. It is held in place by the elastic ring 40. One end of the key 44 is engageable with a cam 14a provided within the upper body 14, as shown in FIG. 5b. The other end thereof is engageable with slots 38b formed within the tens counter ring 38. The configurations of the cam 14a, the slots 38b, and the end of the key engageable with the slots is the same, i.e., triangular.

The transparent housing 18 is adapted for receiving a cartridge 46 of the type including an internal piston 46b and a pierceable seal 46a at one end thereof. Both ends of the transparent housing are threaded. One threaded end 18a is employed for connecting it to the center body 16. The other threaded end 18b is employed for securing a double ended needle assembly 50. Needle assembly 50 includes a cannula 50a having a sharp distal end 50b for piercing the skin of the user and a sharp proximal end 50c for piercing seal 46a of the cartridge and a lumen (not shown) therethrough. Needle assembly 50 includes a cup shaped hub 50d holding said cannula so that the sharp proximal end projects outwardly from the interior of the cup-shaped hub. The cup-shaped hub includes an internal thread which is compatible with the thread at 18a so that the needle assembly may be removably attached to housing 18 with its sharp proximal end piercing pierceable seal 46a to establish fluid communication between said lumen and the interior of said cartridge.

The operation of the injection device 10 shall now be described with reference to the accompanying figures. Generally speaking, a cartridge is loaded within the device, and a double ended needle is affixed to the end of the transparent housing. Fluid communication is accordingly established between the injection portion of the double ended needle and the interior of the cartridge. Once the appropriate dosage is set, the push button 24 is urged forwardly, causing the lead screw 26 to exert pressure upon the piston movably positioned within the cartridge. The piston displaces fluid within the cartridge, causing its injection into body tissue through the double ended needle. The specific functions which are performed using the injection device are described separately herein. Assuming the device is loaded, three steps are followed in the injection procedure: set to zero, set the dose, and make the injection.

TO SET TO ZERO

The adjusting knob 12 is rotated back to the zero setting on both counter rings 36 and 38. As will be described in more detail hereinbelow, the adjusting knob turns the units counter ring 36 and the tens counter ring 38. Because the splines on the units counter ring 36 and the plunger 22 are disengaged, as shown in FIG. 7, the plunger 22 and the lead screw 26 do not turn. When the rings reach zero, their slots align as shown in FIG. 8 and release the upper spring member 42e of the zero detection clip 42. This in turn releases the plunger 22 and push button 24 which move open under pressure from the spring 32 through the two half nuts 28 until the nuts reach the stop on the zero detection clip 42. This movement also carries the lead screw 26. The ribs 22b on the plunger 22 engage with the splined units counter ring 36 ready for setting a dose.

TO SET THE DOSE

The adjusting knob 12 is rotated away from the zero (0) setting. The adjusting knob turns the units counter ring 36, which turns the plunger 22. The plunger 22 is engaged with the longitudinal grooves 26d in the lead screw 26 which turns and screws forward in the nut formed by the two half nuts 28. The lead screw's travel is proportional to the number of units displayed by the counter rings 36, 38.

TO MAKE AN INJECTION

When the desired dose has been set, the push button 24 is pushed fully in. The push button 24 pushes the plunger 22, the two half nuts 28, and the lead screw 26 forwards. The plunger and lead screw, as coupled by the half nuts, accordingly perform the function of a piston rod. The travel is determined by the bosses of the two half nuts 28 which slide in slots inside the center body 16 up to a stop defined by the rear end of the locking ring 30. The travel corresponds to the maximum dose which can be injected. The first part of the travel brings the end of the lead screw 26 into contact with the piston 46b of the cartridge 46; the second part of the travel moves the piston of the cartridge forward and delivers the measured amount of insulin. While setting the dose, the lead screw 26 is moved forward in proportion to the dosage set; this distance determines the proportion of the pre injection and injection travel. The plunger and the push button are locked in position by the upper spring member of the zero detection clip 42 following an injection.

EXAMPLES

If the dose is set to 0 units, the lead screw 26 will not touch the piston of the cartridge until the end of the travel and no units will be injected. (Pre travel 59, injection travel 0.)

If the dose is set to 59 units, the lead screw will touch the piston of the cartridge immediately and 59 units will be injected. (Pre travel 0, injection travel 59.)

If the dose is set to "n" units, the lead screw will move forward 59−n units until it touches the piston of the cartridge, and then push the piston forwards 59−(59−n−)=n units. (Pre-travel 59−n, injection travel n.)

DOSE SETTING FOR PARTIALLY SIGHTED USERS

When a dose is set, the units counter ring 36 pushes the upper spring member 42e of the zero detection clip 42 into its active position. The ridge 42f on its inner surface creates a click for each unit as it passes over the splines (ribs 22b) on the plunger 22. The units counter ring 36 drives the tens counter ring 38 through 36 degrees of rotation every time the units counter ring passes zero. The lower spring member 42c of the zero detection clip 42 has a ridge 42d which engages with the grooves 38a inside the tens counter ring 38 and creates a click every time the tens counter ring 38 turns. The clicks of the two counter rings coincide every ten units, making an accentuated click to help partially sighted users.

LIMITATION OF DOSE

If the dose is set at 59 units, the tens counter ring 38 reaches a stop, and the transmission key 44 engage in the last location in the tens counter ring 38 as shown in FIG. 11. If the adjusting knob 12 is turned further, the rings 36 and 38 are unable to turn, and the adjusting knob 12 slips without further effect. The rounded shapes of the ribs 22b in the grooves (splines) of the units counter ring 36 limit the torque which will be transmitted to the counter rings and prevent unintentional damage.

LIMITATION OF DOSE TO THE REMAINING CAPACITY OF THE CARTRIDGE

The travel of the lead screw 26 is limited to the safe travel of the piston in the cartridge 46. If the lead screw 26 reaches the end of its travel, the projections 22c inside the plunger 22 reach the end of the grooves 26d in the lead screw 26 and prevent it from further movement. The lead screw 26 prevents the plunger 22 and the counter rings 36 and 38 from turning. The adjusting knob 12 will then slip without further effect. The counter rings will indicate the travel of the lead screw to this point, and, therefore, the quantity of insulin remaining in the cartridge.

CHECKING THE REMAINING CAPACITY OF THE CARTRIDGE

The adjusting knob 12 is rotated away from the zero (0) setting. If there are more than 59 units remaining in the cartridge, the counter rings will stop at 59 units as described above. If there are less than 59 units remaining, the counter rings will stop as described above and display the remaining capacity of the cartridge.

In either case, the user can then turn the adjusting knob 12 towards himself until the counter rings display the dose to be administered.

CHANGING THE CARTRIDGE

After a complete injection has been made, the push button 24 is left in the locked position. The transparent housing 18 is unscrewed and the cartridge is removed.

The transparent housing 18 has two recesses 18a which engage with the projections 30c extending from the locking ring 30. When the transparent housing 18 is unscrewed, the locking ring 30 is turned through 90 degrees before disengaging. The locking ring 30 meets two stops 16a inside the center body 16 which prevent it from turning further.

The elliptical shape defined by the inner wall of the locking ring 30 allows the two half nuts 28 to open under pressure from the spring 32 and to free the lead screw 26 as shown in FIG. 9.

A new cartridge 46 is inserted into the transparent housing 18 which is then screwed into place. As the transparent housing 18 moves towards the center body 16, the piston of the cartridge will push the lead screw 26 into the device. About 90 degrees before the end of its travel, the two recesses of the transparent housing 10 engage with the projections of the locking ring 30 and turn it through 90 degrees. The locking ring 9 meets the two stops inside the center body 16 which prevent it from turning further. The elliptical inner wall of the locking ring 30 moves the two half nuts 28 into engagement with the lead screw 26. The thread profile is adapted to this engagement.

The position of the lead screw 26 is determined by the position of the piston in the cartridge. when the first dose is set, the lead screw 26 will be in the correct relative position to make an immediate injection. It is thus possible to load partially filed cartridges if desired.

OPERATION OF THE COUNTER RINGS

The upper body 14 houses the four parts which comprise the counter mechanism. The window 34 in the upper body 14 shows the numbers printed on the out-side of the two counter rings 36 and 38, and indicates the number of units to be injected from 0 to 59.

The units counter ring 36 is turned by the adjusting knob 12. When the units counter ring 36 has turned to numbered position "8", the transmission key 44 meets the cam 14a molded inside the upper body 14. The transmissions key 44 is forced to side up the face of the cam, and reaches the top in position "9". The elastic ring 40 is deformed by this movement and maintains the transmission key 44 in contact with the cam. This movement also brings the opposite end of the transmission key 44 into engagement with one of the slots 38b inside the tens counter ring 5.

When the units counter ring 36 is turned further, the transmission key 44 transmits the movement to the tens counter ring 38, and the two rings turn together. At position "10" the window 34 now displays "10". At this point, the transmission key 44 has rotated 36 degrees to the end of the raised face of the cam inside the upper body 14.

If the units counter ring 36 is turned further, the transmission key 44 is free to slide down the face of the cam 14a inside the upper body 14 under pressure from the elastic ring 40. This movement disengages the two counter rings, and the counter will now read "11".

This movement is repeated each time the units counter ring 36 moves from position "8", through positions "9" and "0" to position "1". The reverse procedure is identical.

The tens counter ring 38 has stops in the "0" and "5" positions to prevent the counter mechanism from going beyond a maximum reading of 59 or a minimum reading of 0 units. In both of these positions the transmission key 44 is in its active, engaged position, which explains why it has seven slots.

It should be noted that if the stops for the tens counter ring 38 were moved, the reading could continue up to 99 units.

OPERATION OF THE ZERO DETECTION CLIP

The upper spring member 42e of the zero detection clip 42 is the key to the alternate "count/reset" movement of the injection device 10.

The upper spring member 42e pushes up in its relaxed position, as shown in FIG. 8. The two counter rings 36 and 38 have slots which align in the zero (0) setting position and which allow this movement.

The slot in the units counter ring 36 has an angled face which works as a cam, forcing the upper spring member 42e down into its active position as soon as the units counter ring 36 leaves the "0" position. The units counter ring 36 holds the zero detection clip 42 in its active position up to position "9". In position "10" the tens counter ring 38 has moved, and now holds the zero detection clip 6 in its active position. From position "10" to position "59" the zero detection clip 42 is held in its active position by the tens counter ring 38. FIG. 7 illustrates the engagement of the tens counter ring with the spring member 42e, while FIG. 9 illustrates the engagement of the units counter ring therewith.

In its active position, the underside of the zero detection clip 42 is in contact with the splines (ribs 22b) on the plunger 22. The ridge 42f under the upper spring member fits between the ribs 22b and ensures their indexation. The ridge 42f also makes the click sound as each rib 22b passes while a dosage adjustment is made. When an injection is made, the plunger 22 slides through the zero detection clip 42 until the ends of its travel. At this point the end of the upper spring member 42e drops behind the end of the rib 22b and prevents the plunger 22 from moving out under pressure from the spring 32. The components can be designed so that this movement will make a clicking sound, confirming that a complete injection has been made.

When the counter is set to "0" as shown in FIG. 8, the slots inside the two counter rings 36 and 38 align with the upper spring member of the zero detection clip 42 and allow it to spring up into its rest position. This movement frees the plunger 22 and allows a new dose to be set.

The injection device as constructed in accordance with the invention offers a number of desirable features which facilitate its use. The size of the device, including a relatively short length and small diameter, allows it to be easily carried and used. A clip (not shown) may be provided in order to secure the device to a pocket.

The cartridge 46 is easily loaded and substantially fully visible to the user. Two-way dosage adjustment is possible, which allows corrections to be made quickly and easily. The dosage to be administered is clearly displayed and will remain displayed subsequent to the injection procedure. In order to insure that a complete injection has been made, the device produces a click and locks in the closed position only when the plunger is fully inserted.

Although illustrative embodiments of the present invention have been described herein with reference to the accompanying drawings, it is to be understood that the invention is not limited to those precise embodiments, and that various other changes and modifications may be effected therein by one skilled in the art without departing from the scope of the invention.

What is claimed is:

1. An injection device for injecting selected dosages of fluid, comprising:
   an elongate housing;
   a manually operable plunger positioned at least partially within said housing and axially movable within said housing;
   a lead screw having external threads positioned at least partially within said plunger and axially slidable therein;
   means for threadably engaging said lead screw;
   means for selectively moving said means for threadably engaging said lead screw into and out of engagement with said lead screw, whereby said lead screw is freely slidable with respect to said plunger when said means for threadably engaging said lead screw is disengaged from said lead screw, said lead screw and plunger being slidable as a unit with respect to said housing when said means for threadably engaging said lead screw is engaged with said lead screw;
   means for securing a fluid containing cartridge having an internal piston to said housing so that said lead screw can move said piston, said means for securing a cartridge being engageable with said means for selectively moving such that said lead screw is disengaged from said means for threadably engaging said lead screw when said means for securing is disengaged from said housing; and
   wherein manual force applied to said plunger, when said means for threadably engaging said lead screw is engaged with said lead screw, is transferred to said lead screw for moving said piston to expel fluid from said cartridge.

2. A device as described in claim 1 wherein said means for securing a cartridge to said housing is an elongate cartridge housing having an end portion securable to said housing.

3. A device as described in claim 2 wherein said means for threadably engaging said lead screw includes a pair of at least partially threaded half nuts positioned in opposing relation to each other within said housing with the threaded portion of said half nuts facing said lead screw, and said means for moving include a rotatable locking ring, said locking ring including an internal wall defining a plurality of diameters, said half nuts engaging said internal wall of said locking ring, said locking ring being engageable with said cartridge housing such that rotation of said cartridge housing causes rotation of said locking ring with respect to said half nuts.

4. A device as described in claim 3 including means for resiliently urging said locking ring and half nuts in opposing axial directions.

5. A device as described in claim 4 including means for uring an end of each half nut radially inwardly.

6. A device as described in claim 5 wherein said half nuts are coupled to said plunger such that said half nuts and said plunger are slidable as a unit within said housing.

7. A device as described in claim 6 including means for abutting said half nuts at a selected axial position within said housing.

8. A device as described in claim 7 wherein said plunger includes a band of radially extending ribs, said band including a first end portion which abuts against said half nuts and a second end portion, said means for abutting said half nuts including a spring member mounted within said housing, said spring member abutting against said half nuts when said plunger is in a first axial position with respect to said housing and abutting against the second end portion of said band of ribs when said plunger is in a second axial position.

9. An injection device as described in claim 1 further including an elongate fluid-containing cartridge having an internal piston at its proximal end and a pierceable seal at its distal end defining a reservoir for said fluid, said cartridge being secured to said housing.

10. An injection device as described in claim 9 further comprising a needle assembly including an elongate cannula and a cup-shaped hub, said cannula having a sharp proximal end, a sharp distal end and a lumen therethrough, said cup shaped hub holding said cannula so that said sharp proximal end of said cannula projects outwardly from the interior of said cup-shaped hub, said needle assembly being removably attached to said device so that said sharp proximal end pierces said pierceable seal of said cartridge so that said lumen is in fluid communication with the fluid in said cartridge.

* * * * *